(12) United States Patent
Videen

(10) Patent No.: US 7,355,707 B1
(45) Date of Patent: Apr. 8, 2008

(54) SYSTEMS AND METHODS FOR ANALYZING DEW IN A SYSTEM OF INTEREST

(75) Inventor: Gorden Videen, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 187 days.

(21) Appl. No.: 11/223,250

(22) Filed: Sep. 9, 2005

(51) Int. Cl.
*G01J 4/00* (2006.01)
(52) U.S. Cl. ...................................... 356/364; 356/128
(58) Field of Classification Search ................ 356/364, 356/128; 250/269.1
See application file for complete search history.

(56) References Cited

U.S. PATENT DOCUMENTS 3,612,689 A * 10/1971 Liskowitz ................... 356/342
6,636,752 B1 * 10/2003 Madarasz et al. ........... 600/310
2001/0048078 A1 * 12/2001 Stair et al. ................... 250/340
2004/0000636 A1 * 1/2004 Mullins et al. ........... 250/269.1

* cited by examiner

*Primary Examiner*—Gregory Toatley
*Assistant Examiner*—Tri Ton
(74) *Attorney, Agent, or Firm*—William W. Randolph; Richard A. Morgan

(57) ABSTRACT

A system and method and for analyzing dew in a system of interest are provided. A representative method comprises receiving infrared information corresponding to a degree of polarization of dew in a particular environment, and using the degree of polarization to determine dew presence in the environment. Changes in the degree of polarization can be attributed to changes in the density, size or shadowing of the dew drops. Infrared emissions information can be detected and accumulated over a range of emission angles and over a period of time. The system compares the accumulated data for the particular environment to detect the presence of dew, the rate of growth of the dew and the change in characteristics of dew over a period of time starting from a first time interval. The system also compares the accumulated data with other previous accumulated data from the environment to detect if changes should be made to the environment.

8 Claims, 4 Drawing Sheets

SYSTEMS AND METHODS FOR ANALYZING DEW IN A SYSTEM OF INTEREST

GOVERNMENT INTEREST

The invention described herein may be manufactured, used, and licensed by or for the United States Government.

BACKGROUND

1. Technical Field

The present disclosure relates generally to remote sensing. In particular, the disclosure relates to analysis of emissions of a system of interest to determine the presence of dew.

2. Description of the Related Art

Polarization emissivity provides a means of remote sensing systems that have some preferential orientation. See, for example, J. A. Shaw, "Degree of linear polarization in spectral radiances from water-viewing infrared radiometers," Appl. Opt. 38, 3157-3165 (1999); P. C. Y. Chang, J. C. Flitton, K. I. Hopcraft, E. Jakeman, D. Jordan, and J. G. Walker, "Importance of shadowing and multiple reflections in emission polarization," Waves Random Media 12, 1-19 (2002); D. L. Jordan, G. D. Lewis, and E. Jakeman, "Emission polarization of roughened glass and aluminum surfaces," Appl. Opt. 35, 3583-3590 (1996); S. V. Nghiem, M. E. Veysoglu, J. A. Kong, and R. T. Shin, "Polarimetric passive remote sensing of a periodic soil surface: microwave measurements and analysis," J. Electromagn. Waves Appl. 5, 997-1005 (1991); R. D. Tooley, "Man-made target detection using infrared polarization," in *Polarization considerations for optical systems II*, R. A. Chipman, ed., Proc. SPIE 1166, 52-58 (1989); and A. W. Cooper, W. J. Lentz, and P. L. Walker, "Infrared polarization ship images and contrast in the MAPTIP experiment," in *Image Propagation Through the Atmosphere*, L. R. Bissonnette and C. Dainty, eds., Proc. SPIE 2828, 35-96 (1996), each of which is incorporated by reference herein. Polarization emissivity has been proposed as a means, for instance, of discriminating between natural and man-made objects. Applications also include surface characterization, like terrain, but especially ocean waves.

U.S. patents and patent applications filed by Gorden Videen include the following; U.S. Pat. No. 6,138,083 (Videen); U.S. Pat. No. 6,239,873 (Videen), U.S. Pat. No. 6,411,441 (Videen); and U.S. Pat. No. 6,414,797 (Videen), U.S. patent application Ser. No. 10/642,676 filed Aug. 19, 2003 by Gordon Videen, entitled Systems And Methods For Analyzing Particle Systems Using Polarized Scattered Lights; U.S. patent application Ser. No. 10/642,677 filed Aug. 19, 2003 by Gordon Videen, entitled Systems And Methods For Analyzing Particle Systems Of Surface Facets Using Polarized Scattered Light; and a U.S. patent application Ser. No. 11/211,560 filed Aug. 20, 2005 and entitled "Systems And Methods For Analyzing Polarized Light Scattered From A Sample", all of which are incorporated by reference herein.

The presence of moisture and dew in various systems have been detrimental in a variety of situations such as accelerating the formation of mold and fungi in grain elevators, animal feeds, and hay lofts; the growth and harvesting of plants and crops; electrical leakage and failure of electrical power equipment, microelectronic equipment and circuit boards; formation of films on optical equipment and retro-reflective surfaces; adverse effects on chemical processes, and the formation of moisture, films and ice on airplanes and vehicle windows. Methods and apparatus for detecting the presence of dew or moisture on surfaces are disclosed in U.S. Pat. Nos. 4,871,917 (O'Farrell et. al.); 4,942,364 (Nishijima et al.); 4,956,591 (Schierbeek et. al.); 5,298,750 (Rericha); 5,433,106 (Matsumura et. al.); 5,483, 346 (Butzer); 5,541,733 (Gagnon); 5,557,251 (Barbour); 6,307,198 (Asakura et. al.); 6,762,409 (Fritsch); 6,768,422 (Schofield et. al.) and 6,832,507 (van de Berg, et. al.); all of which are herein fully incorporated by reference.

SUMMARY

Systems and methods for analyzing dew in a system of interest or an environment are provided. An embodiment of a method comprises the steps of: receiving information corresponding to a degree of polarization of a system of interest; and using the degree of polarization to determine the presence of dew in the system of interest.

Another embodiment of a method comprises the steps of: providing a system model, the system model embodying emission characteristics attributable to dew presence in a system of interest; acquiring information corresponding to light emissions from a system of interest at a first emission angle; determining a degree of polarization of the emissions; and evaluating the degree of polarization of the emissions with the information corresponding to the system model.

An embodiment of a system for analyzing dew in a system of interest comprises a system model embodying infrared (IR) emission characteristics attributable to dew presence in a system of interest.

A further embodiment of the present invention comprises a system and method for detecting the presence of dew and measuring the rate of growth of dew in a particular system of interest.

Other devices, systems, methods, features and/or advantages will be or may become apparent to one with skill in the art upon examination of the following drawings and detailed description. It is intended that all such additional devices, systems, methods, features and/or advantages be included within this description.

BRIEF DESCRIPTION OF THE DRAWINGS

Many aspects of the disclosure can be better understood with reference to the following drawings, where the components in the drawings are not necessarily to scale. Like reference numerals designate corresponding parts throughout the several views and drawings.

DETAILED DESCRIPTION

As will be described in detail here, systems and methods can be used for determining the presence and/or characteristics of dew in a system of interest. Specifically, blackbody radiation, such as infrared (IR) emissions, from a system of interest is analyzed and the polarization of the radiation is evaluated. In general, everything emits radiation. The hotter an object is, the more radiation is emitted and the shorter the wavelength of the emission. For normal room temperatures, for example, the radiation is emitted at infrared wavelengths of on the order of 10 microns. Detectors are used for measuring this radiation. Polarization of the emissions is evaluated with respect to a system model that embodies the behavior of various systems of interest. A representative embodiment of such a system is described below.

In the embodiment described here, the infrared polarization emissivity is modeled for spherical particles on a plane surface. The emissivity and polarization are primarily functions of the density of spherical particles multiplied by their cross-sectional area. The presence of spherical particles tends to reduce the polarization. As the emission angle increases from a near normal incidence, the polarization tends to increase followed by rapid changes such as a sharp rise at near the grazing angles, e.g., where the emission angle approaches ninety degrees from the normal to the surface, approaching ninety degrees from the normal. The mechanism for this structure is the shadowing of different portions of the spherical particles by other particles. Shadowing refers to the inability of rays to travel in a straight line, such as from one portion of the system to the detector, because another portion of the system obstructs the rays.

The motivation for this invention is an anormaly in the polarization emissivity seen in the early hours of the morning around dawn. Experimental observations show a steady decrease in the polarization emissivity, followed by an increase. A natural candidate that can account for this signal is the formation of dew on a surface. Dew particles are approximately spherical. Having no preferential orientation, their net polarization emissivity is zero, regardless of viewing angle. This zero contribution reduces the overall polarization signal from the system, and may be considered a noise term. However, continued growth of dew particles eventually leads them to shadow other dew particles, which breaks symmetry. Ultimately, they come into contact with other dew particles, resulting in a water sheath covering the surface. This smooth water surface has a large polarization signal. Modeling of this effect will now be described.

Figure 1:
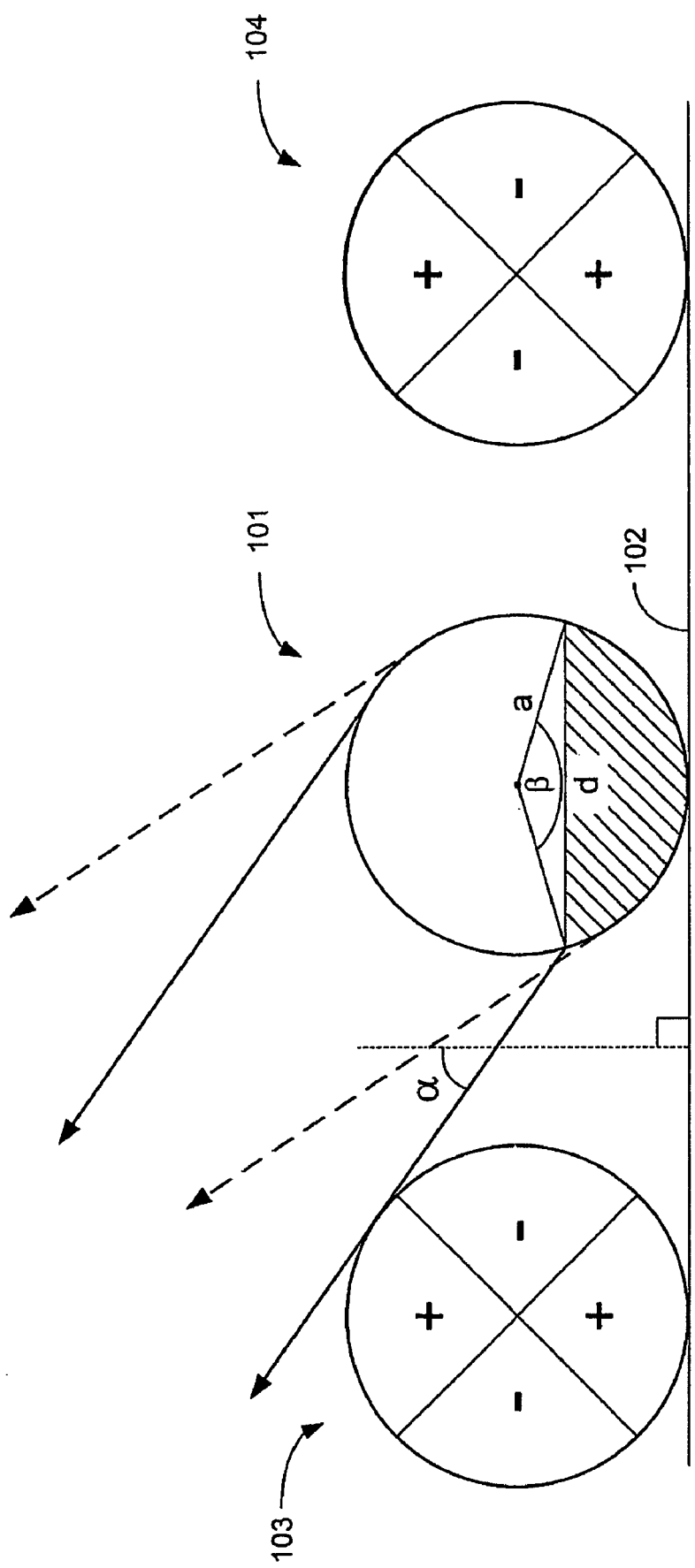
FIG. 1 is a schematic diagram depicting dew drops on a surface.

We begin by considering the effect of a single, isolated sphere on a plane surface, such as depicted in FIG. 1. The dew droplet 101 of radius (a) has a refractive index ($m_d$), and rests on a plane substrate 102 of area (A), refractive index ($m_s$), and ($\alpha$) is the angle of the propagation vector of emitted photons with respect to the surface normal, as shown in FIG. 1. In FIG. 1, the solid-lined rays are emitted at one emission angle $\alpha$ and the dashed-lined rays are emitted at a smaller emission angle. The figure is intended to demonstrate that shadowing is more of a factor at large emission angles, where less of the planar surface of substrate 102 can be seen by a detector because the dew particles cast larger and longer shadows at larger angles.

Each polarization component of the emitted radiation from a surface element (dA) is calculated as $$dI^{T*} = (1 - R^{T*})dA \qquad (1)$$

where each reflectivity component ($R^{T*}$) is given by $$R^{TE}(m, \theta_{dA}) = \left| \frac{\cos\theta_{dA} - m[1 - (1/m)^2 \sin^2\theta_{dA}]^{1/2}}{\cos\theta_{dA} + m[1 - (1/m)^2 \sin^2\theta_{dA}]^{1/2}} \right|^2 \qquad (2)$$

and where m is the refractive index of the material, and $\theta_{dA}$ is the angle between the surface element normal and the direction of propagation of the radiation, angle $\alpha$. We assume no ray interactions and consider the components due to the sphere and the plane surface separately. The contribution of the plane surface to the intensity of each polarization component can be written as $$I^{T*} = [1 - R^{T*}(m, \alpha)](A - S) \qquad (4)$$

where S is the portion of the surface that is shadowed by the sphere. For $A \gg \pi a^2$, $S \to \pi a^2 / \cos\alpha$.

The contribution of the sphere can be calculated by integrating the individual polarization components of Eqn. 1 over the sphere surface visible to the observer:

$$\begin{pmatrix} I^{TE} \\ I^{TM} \end{pmatrix} = \qquad (5)$$

$$\int_0^{2\pi} \int_0^{2/\pi} \left[ \begin{pmatrix} 1 - R^{TE}(m, \varepsilon) \\ 1 - R^{TM}(m, \varepsilon) \end{pmatrix} \begin{pmatrix} \cos^2\phi & \sin^2\phi \\ \sin^2\phi & \cos^2\phi \end{pmatrix} \right] a^2 \cos\varepsilon \sin\varepsilon d\varepsilon d\phi$$

where $\epsilon$ is the spherical polar angle drawn from the line of sight from the sphere to the observer. TE is the transverse-electric component and TM is the transverse-magnetic component. The degree of polarization is given by $$P = \frac{I^{TE} - I^{TM}}{I^{TE} + I^{TM}}. \qquad (6)$$

Note that because of symmetry, the polarization component from the sphere by itself in the Eqn. 5 is zero. The larger the size of the sphere, the larger the emissive intensity of this zero-polarization contribution, and the lower the polarization of the entire system.

Complications arise when there are multiple spheres. As non-normal observation angles $\alpha$ are considered, these spheres may shadow each other, affecting their contribution to the polarization signal. For example, as shown in FIG. 1, dew drop 103 partially shadows dew drop 101 at the emission angle defined by the solid-lined rays. This shadowing may increase the signal because 1) more of the plane surface is visible than if the spherical particles were isolated and 2) only a portion of the dew droplet contributes to the signal. FIG. 1 also illustrates this latter point. Specifically, FIG. 1 displays the signs of the contributions of the dew droplets 103 and 104 to the polarization signal. Because emission angles from the centers of the dew droplets are at near-normal incidence, they have little polarization. At the edges, where the angles are steeper, the resulting polarization has higher magnitude.

The upper and lower portions of the dew droplets contribute to positive polarization, and the right and left sides contribute to negative polarizations. A shadow over only part of a dew droplet removes its contribution to the total signal. The amount of shadowing depends on the observation angle $\alpha$, the sizes a (radius a), number density $\rho = N$ (number of dew particles)/A (unit area of the plane surface), and relative positions of the spheres. This is also illustrated in FIG. 1. The sphere component of the polarization signal is $$\begin{pmatrix} I^{TE} \\ I^{TM} \end{pmatrix} = \tag{7}$$

$$\int_0^{2\pi} \int_0^{2\pi} \delta_U \left[ \begin{pmatrix} 1 - R^{TE}(m,\varepsilon) \\ 1 - R^{TM}(m,\varepsilon) \end{pmatrix} \begin{pmatrix} \cos^2\phi & \sin^2\phi \\ \sin^2\phi & \cos^2\phi \end{pmatrix} \right] a^2 \cos\varepsilon \sin\varepsilon d\varepsilon d\phi$$

where $\delta_u = 1$ on regions of the sphere that are unshadowed and $\delta_u = 0$ on regions that are shadowed.

The greatest challenge in achieving numerical results is quantifying the nature of the shadowing. This is especially true when dealing with a large number of particles, like dew on a surface. In this study, we assume a monodisperse distribution on sphere size. The approach we take to account for the shadowing of spheres by other spheres is indirect. We first consider the shadowing on the plane surface. The unshadowed area of the plane surface $$A_{UP} = A - N\pi a^2 / \cos\alpha + A_{MP}, \tag{8}$$

where $A_{MP}$ is the area of the plane surface element that is shadowed by more than one sphere. The area of the shadow of a sphere that can cast a shadow on another sphere shadow is $A_{SS} = N\pi a^2(1/\cos\alpha - 1)$. We assume the percentage of $A_{SS}$ falling on a shadowed region is determined by the area of the surface covered in shadow, i.e., $A_{MP} = A_{SS}(A - A_{UP})/A$.

We solve for $$A_{MP} = \frac{A_{SS}(N\pi a^2/\cos\alpha)}{A + A_{SS}} \tag{9}$$

so that the proportion of areas that is shadowed by multiple spheres is $$A_{MP}/A = \rho^2 \pi^2 a^4 \frac{-1 + \cos\alpha}{(\cos\alpha)(-\cos\alpha - \rho\pi a^2 + \rho\pi a^2 \cos\alpha)} \tag{10}$$

and the proportion of area that is unshadowed is $$A_{UP}/A = \frac{\cos\alpha(1 - \rho\pi a^2)}{\rho\pi a^2 + \cos\alpha(1 - \rho\pi a^2)}. \tag{11}$$

The polarization contribution of the unshadowed portion of the plane surface can be calculated directly from Eqn. 4. We can find the contribution of the spheres by considering how efficiently they cast shadows on the plane surface. The efficiency E of spheres casting a shadow on the plane surface is equal to the area of the plane surface shadowed divided by the potential amount of shadow cast by the spheres, i.e.

$$E = 1 - \frac{A_{MP}}{N\pi a^2/\cos\alpha} = 1 - \rho\pi a^2 \frac{-1 + \cos\alpha}{(-\cos\alpha - \rho\pi a^2 + \rho\pi a^2 \cos\alpha)}. \tag{12}$$

We assume that the shadows cast on all spheres are approximately the same and the shapes of the shadows are bounded by chord line segments d, that are parallel to the line surface as shown in FIG. 1. The area of this shadowed region of the projected sphere is $$A_{CS} = \frac{a^2}{2}(\beta - \sin\beta),$$

where $\beta$ is the angle extended to the ends of the chord from the center of the sphere. The efficiency E can also be expressed as $$E = \frac{\pi a^2 - A_{CS}}{\pi a^2} = \frac{2\pi - (\beta - \sin\beta)}{2\pi}. \tag{13}$$

Equations 12 and 13 provide a means of determining the area of the unshadowed sphere to integrate over in Eqn. 7.

Figure 2:
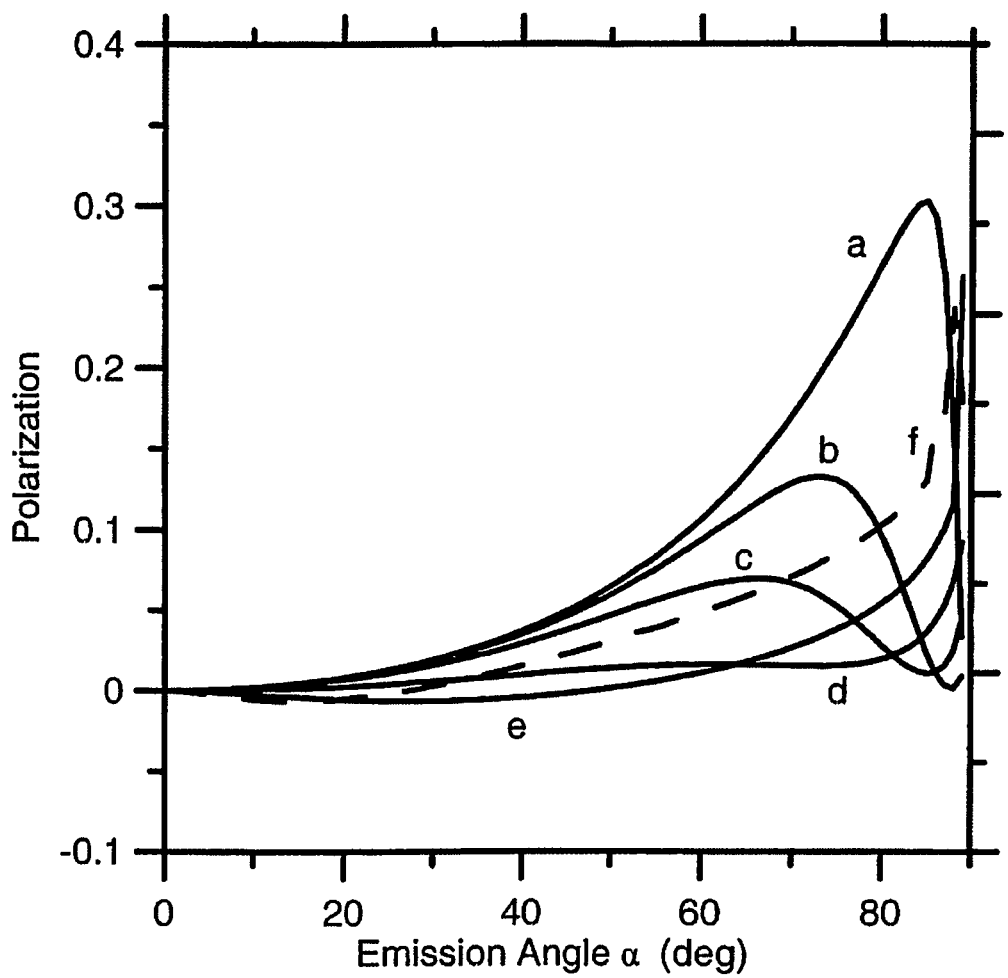
FIG. 2 is a graph of emission polarization versus emission angle for dew drops of various parameters.

FIG. 2 shows results of calculations of spherical water ($m_d$=1.33) droplets on a dielectric ($m_s$=1.55) substrate for six different dew density-sizes $\rho\ a^2$; specifically, emission polarization P (a) for $\rho\ a^2$=0.0001 (a), 0.01 (b), 0.04 (c) 0.16 (d), 0.64 (e), 2.56 (f) planar sheath. For the smallest density-sizes ($\rho\ a^2$=0.0001), the polarization state is almost entirely dominated by the plane substrate except at large emission angles. It is only then, due to their increased projected area, that the droplets play a significant role. As $\rho\ a^2$ increases, the magnitude of the polarization state tends to decrease at near normal emission angles, but additional structure creeps into the curves at larger emission angles. This is a result of the shadowing of the spheres by other spheres. Shadowing truncates the contribution of the lower quadrant, reducing its positive contribution. As the middle becomes truncated, the droplets' polarization contribution passes through zero and then becomes positive again when the top quadrant is the primary contributor. The net effect on the polarization curve is a maximum, which moves to smaller emission angles as $\rho\ a^2$ increases. This is followed by a very deep minimum that may be negative. At very large emission angles near $\alpha$=90°, the signal may again be strongly positive, the result of contribution from only the top portions of the droplets.

Finally, we should note that two cases shown in FIG. 2 ($\rho\ a^2$=0.64, 2.56), represent situations where the droplets' projected area is greater than that of the surface, i.e., the droplets shadow each other as well as the plane surface, even at normal incidence. In this case, the model represents the emission from a surface consisting of the rounded tops of the spheres. While this is certainly not the best model of the surface morphology which we would expect to be a near planar sheath, it may have some instructional benefit. For the largest case, $\rho\ a^2$=2.56, the polarization response is determined from the nearly planar tops of the dew droplets, i.e., only the tops of the droplets have an un-shadowed path to the detector, and we observe that the polarization response increases, similar to that of a plane water surface.

Figure 3:
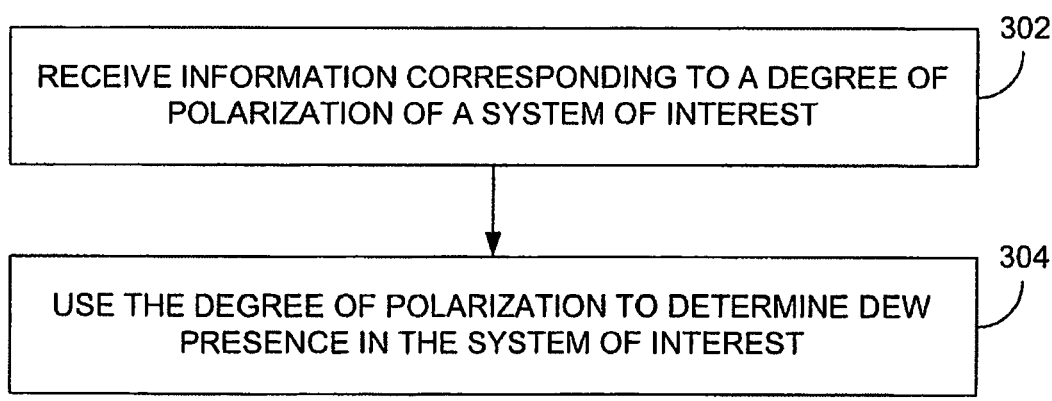
FIG. 3 is a flowchart depicting functionality of an embodiment of a system for analyzing dew in a system of interest.

Reference will now be made to the flowchart of FIG. 3, which depicts functionality of an embodiment of a system for analyzing dew in a system of interest. As shown in block 302, the functionality (or method) may be construed as beginning at block 302, where measurements corresponding to a system of interest are received. In block 304, the measurements are used to estimate a characteristic of this system of interest. Specifically, the information corresponding to a degree of polarization of the system of interest is used to determine the presence of dew in the system. Further, the information can also be used to track the rate of growth of dew in a particular system of interest, such as, for example, on a roadway, an airplane wing, optical surfaces, electrical circuits, chemical equipment, storage facilitates, and agricultural processes.

Figure 4:
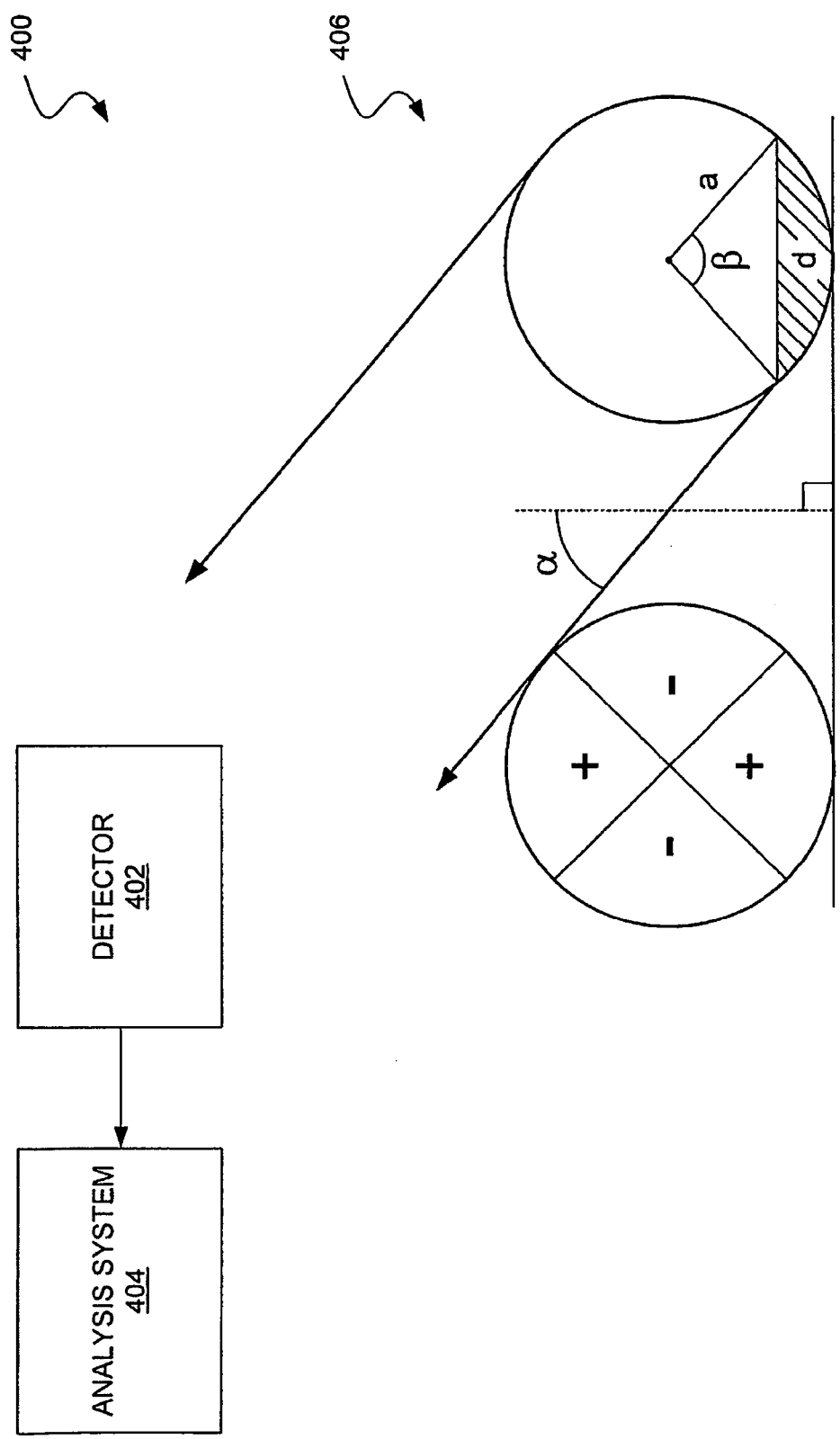
FIG. 4 is a schematic diagram of an embodiment of a system for analyzing dew in a system of interest.

FIG. 4 is a schematic diagram depicting an embodiment of a system for analyzing dew in a system of interest. As shown in FIG. 4, system 400 includes a detector 402 that communicates with an analysis system 404. The detector may be a cooled or uncooled detector of infrared radiation. Such a detector may include means of detecting the two orthogonal polarization states of the infrared emission. This may include a combination of a detector and a polarizer that may be rotated to measure these two polarization states. Alternatively, a detector that measures one polarization state preferentially, or two detectors, each of which is equipped with a polarizer oriented to transmit one of the two polarization states, can be used. By way of further example, a detector equipped with an optical modulator that will allow the polarization state to be measured through its polarization and time-dependent transmission could be used.

Regardless of the particular implementation, the detector acquires information corresponding to emissions of a system of interest, e.g., system of interest 406. Specifically, the detector acquires information corresponding to a degree of polarization of the system over a range of emissivity angles and/or time intervals. The detector provides the information to analysis system 404 so that the presence and/or characteristics of dew in the system of interest can be determined.

Analysis systems, such as analysis system 404 of FIG. 4, can be implemented in software, firmware, hardware, or a combination thereof. When implemented in hardware, an analysis system can be implemented with any or a combination of various technologies. By way of example, the following technologies, which are each well known in the art, can be used: a discrete logic circuit(s) having logic gates for implementing logic functions upon data signals, an application specific integrated circuit (ASIC) having appropriate combinational logic gates, a programmable gate array(s) (PGA), and a field programmable gate array (FPGA).

In alternative embodiments, an analysis system can be implemented in software as an executable program(s). For example, an analysis system can be executed by a special or general purpose digital computer. An example of a computer that can implement such an analysis system is shown schematically in FIG. 5.

Figure 5:
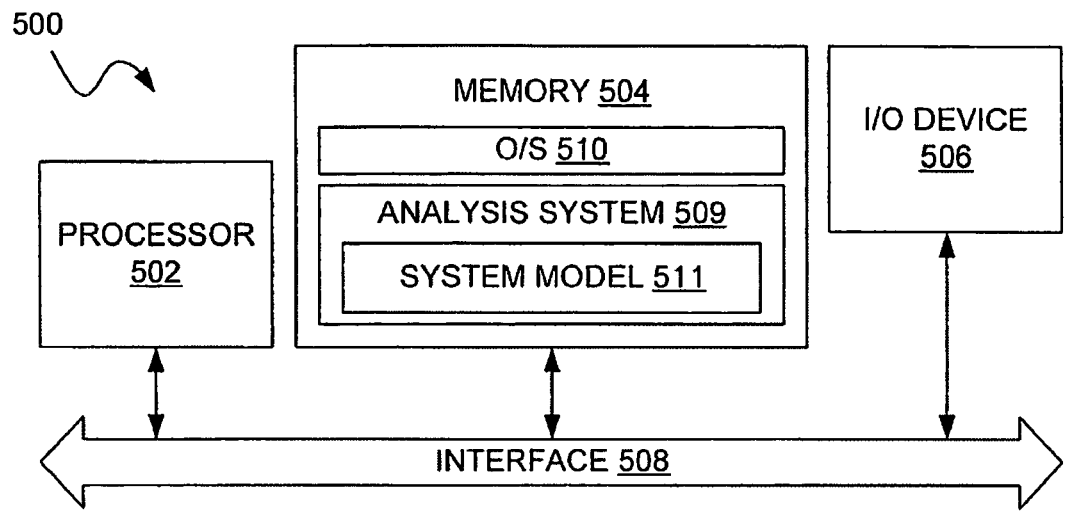
FIG. 5 is a schematic diagram of a computer or processor-based system that can be used to implement a system for analyzing dew in a system of interest.

Generally, in terms of hardware architecture, computer 500 includes a processor 502, memory 504, and one or more input and/or output (I/O) devices 506, such as detector 402 of FIG. 4, that are communicatively coupled via a local interface 508. The software in memory 504 can include one or more separate programs, each of which comprises an ordered listing of executable instructions for implementing logical functions. In the example of FIG. 5, the software in the memory 504 includes an embodiment of an analysis system 509 and an operating system (O/S) 510. Note, analysis system 509 includes a system model 511, which embodies functionality such as described above.

When analysis system 509 is implemented in software, it should be noted that the analysis system can be stored on any computer-readable medium for use by or in connection with any computer-related system or method. In the context of this document, a computer-readable medium is an electronic, magnetic, optical, or other physical device or means that can contain or store a computer program for use by or in connection with a computer-related system or method. An analysis system can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

Reference will now be made to the flowchart of FIG. 6, which depicts functionality of the analysis system 509 of FIG. 5. Note that the functionality associated with one or more of the blocks depicted in FIG. 6, or any other of the accompanying flowcharts, may occur out of the order in which depicted. For instance, the functionality associated with two successive blocks may be performed substantially simultaneously, or in reverse order in some embodiments.

Figure 6:
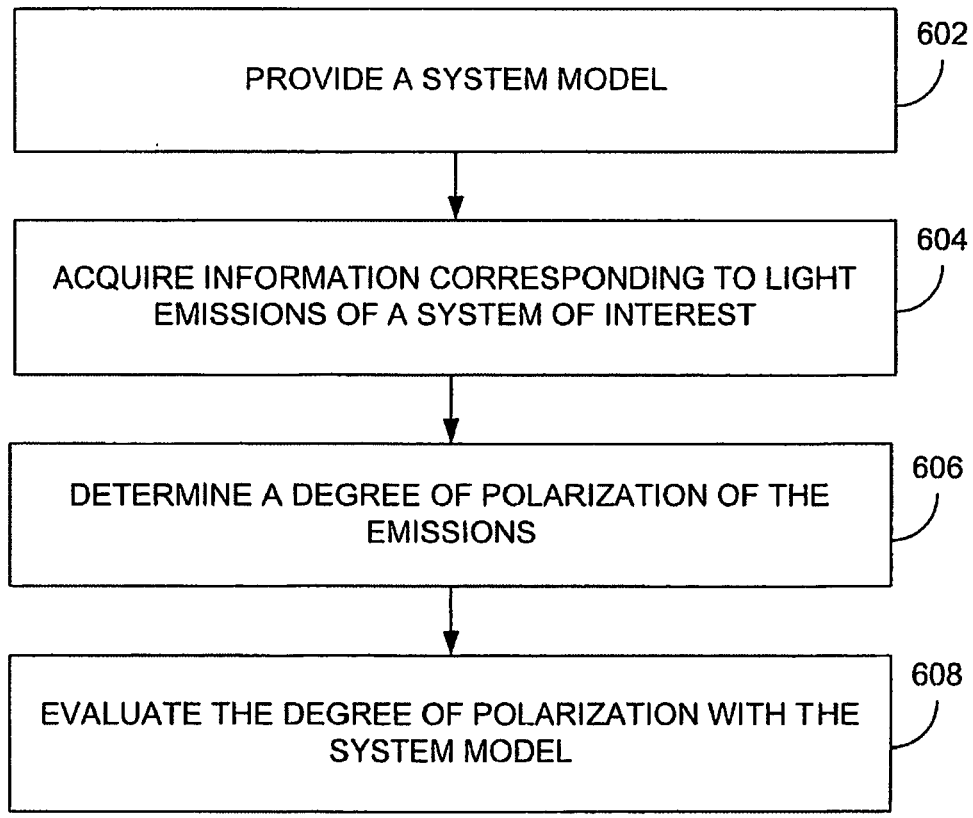
FIG. 6 is a flowchart depicting functionality of an embodiment of a system for analyzing dew in a system of interest.

Referring now to FIG. 6, the functionality (or method) may be construed as beginning at block 502, where a system model is provided. In particular, the system model embodies emission characteristics attributable to dew presence in a system of interest. In block 604, information corresponding to light emissions from a system of interest is acquired at a first emission angle. In block 606, a degree of polarization of the emissions is determined. Then, in block 608, the degree of polarization of the emissions is evaluated with the information corresponding to the system model. By way of example, in evaluating the degree of polarization using the system model, the presence of dew in the system of interest can be determined. Additionally, various characteristics about dew in the system of interest also can be determined. For example, size and number of dew drops can be determined, as described above. Further the computer may be arranged to store historical data for the system of interest so that a particular result can be compared with the historical data starting from the first time interval stored. This allows the computer to track the growth and changes in the dew characteristics over a period of time, and also compare the detected presence of dew in a system with historical data from other previous, similar systems of interest so that appropriate accommodations can be made to the system of interest.

It should be emphasized that many variations and modifications may be made to the above-described embodiments. All such modifications and variations are intended to be included herein within the scope of this disclosure and protected by the following claims.

What is claimed is:

1. A method for analyzing dew in a system of interest, said method comprising the steps of:
   providing a system model, the system model embodying emission characteristics attributable to dew presence in a system of interest;
   acquiring information corresponding to infrared light emissions from a system of interest at a first emission angle during a first time interval;
   determining a degree of polarization of the infrared light emissions; and
   evaluating the degree of polarization of the infrared light emissions with the information corresponding to the system model.

2. The method of claim 1, wherein in evaluating the degree of polarization, a time-dependent aspect of the system model associated with the presence of dew is compared to the information acquired during the first time interval.

3. The method of claim 1, wherein in evaluating the degree of polarization, a reduction in the degree of polarization during the first time interval is attributed to dew forming in the system of interest.

4. The method of claim 1, wherein in providing a system model, the system model attributes a positive polarization contribution to upper and lower portions of a dew drop.

5. The method of claim 1, wherein in providing a system model, the system model attributes a negative polarization contribution to side portions of a dew drop.

6. The method of claim 1, wherein evaluating the degree of polarization of the infrared light emissions comprises the step of:
   determining whether dew is present in the system of interest.

7. The method of claim 6, wherein evaluating the degree of polarization of the infrared light emissions additionally comprises the step of:
   determining at least a first characteristic of the dew, if dew is present in the system of interest;
   then for dew present in the system, accumulating data over a period of time to determine the rate of change in the dew in the system; and
   comparing the accumulated data with historical data for the system of interest to predict expected changes in dew for the system of interest.

8. A system for analyzing dew in a system of interest, said system comprising:
   a system model embodying infrared light emission characteristics attributable to dew presence in a system of interest;
   a detector operative to acquire information corresponding to infrared light emissions of a system of interest and to provide the information for evaluation by the system model;
   an analysis system operative to evaluate information corresponding to infrared light emissions of a system of interest using the system model, the analysis system comprising computer-executable instructions embodied on a computer-readable medium;
   a computer operative to execute the computer-executable instructions of the analysis system; and
   means for executing the computer-executable instructions of the analysis system to detect the presence of dew in the system, the rate of change in the dew over a period of time, and compare the accumulated data over a period of time with previous historical data for the system of interest to predict the expected changes in dew in the system of interest.

* * * * *